United States Patent [19]

Schunk

[11] 4,127,126
[45] Nov. 28, 1978

[54] ORAL DISPENSING DEVICE

[76] Inventor: George J. Schunk, 3265 Azalea Dr. S., Salem, Oreg. 97302

[21] Appl. No.: 740,842

[22] Filed: Nov. 11, 1976

[51] Int. Cl.² ............................................. A61M 1/00
[52] U.S. Cl. .................................... 128/234; 128/239
[58] Field of Search ............... 128/235, 234, 232, 239, 128/241, 245, 260, 261, 224, 222

[56] References Cited

U.S. PATENT DOCUMENTS

| 166,967 | 8/1875 | Clotworthy | 128/234 |
| 1,497,264 | 6/1924 | Gurnee et al. | 128/239 |
| 3,572,337 | 3/1971 | Schunk | 128/234 X |

FOREIGN PATENT DOCUMENTS 543,150  1/1927  Fed. Rep. of Germany ........... 128/239

Primary Examiner—John D. Yasko

Attorney, Agent, or Firm—Kolisch, Hartwell, Dickinson & Stuart

[57] ABSTRACT

A syringe and removable nozzle assembly for the oral administration of liquid medicine or drugs. A syringe body in the assembly includes an elongate, hollow barrel within which is received an elongate plunger for reciprocating a piston. The body further includes a hollow tip which is insertable within a removable nozzle member. The removable nozzle member includes an elongate tube and a lip abutment skirt. The tube is insertable within the mouth of a person to whom the medicine is to be administered, and the skirt prevents mouth contamination with the barrel. After oral administration of the medicine, the nozzle member may be removed for cleansing. The syringe body may be provided with a new or cleansed nozzle member for subsequent use.

7 Claims, 2 Drawing Figures

ORAL DISPENSING DEVICE

BACKGROUND AND SUMMARY OF THE INVENTION

The present invention relates to oral dispensing devices, and more particularly to a syringe for the oral administration of liquid medicine or drugs which includes a syringe body and a removable nozzle member fitted onto the syringe body. The removable nozzle comprises an elongate tube to which is joined a lip abutment skirt. The syringe body includes a tip insertable through the skirt and into a portion of the tube. Medicine may be dispensed through the tube into an individual's mouth.

It has been found advantageous to utilize a syringe for the oral administration of liquid medicine to children, the aged or infirm. Typically, such an oral dispensing device includes an elongate barrel within which is slidably disposed a reciprocating piston. The piston is reciprocated within the barrel by means of an elongate plunger, and the dispensing end of the barrel includes a flexible tip through which the medicine is injected into the mouth. Interposed between the flexible tip and the end of the barrel is a lip abutment skirt. Such a syringe is the subject of applicant's prior issued U.S. Pat. No. 3,572,337.

When it is desired to administer a liquid medicine to a patient, the flexible tip is inserted into a vial or the like containing the liquid and the plunger is withdrawn with liquid then being drawn into the barrel by suction. The flexible tip is then inserted into the corner of the patient's mouth between the cheek and lower teeth. The medicine is administered into the mouth by means of depressing the plunger whereby the medicine is forcibly passed from the barrel through the tip.

The aforementioned lip abutment skirt effectively prevents the mouth of a patient from contacting the syringe barrel, encourages sucking by the patient, and guards against the tip being inserted too far into the patient's mouth. With prior art devices, the entire syringe assemblage must be cleansed before the flexible tip may be inserted into another medicine vial or before it may be inserted into the mouth of another patient.

There are situations both at home and in the hospital where it is required to quickly and efficiently orally administer drugs to more than one patient. If only a single syringe or a limited number of syringes are available, it is readily apparent that time-consuming cleansing may be required between administration of medicine from one patient to another.

Accordingly, the present invention provides a solution to the aforementioned problem by providing a nozzle member which is readily assembled with a syringe body to produce a syringe for the oral administration of medicine. The nozzle member includes an elongate tube connected to a lip abutment skirt. The syringe body includes a tip insertable through the lip abutment skirt and into a portion of the tube. The nozzle member may be readily removed from assembly with the syringe body after the administration of medicine to a patient, for cleansing or disposal. The syringe body may then be inserted into a new or clean nozzle member for the oral administration of medicine to another. The syringe body remains uncontaminated, because the lip abutment skirt of the prior used nozzle member effectively prevents mouth contact with the syringe barrel.

It is a general object of the present invention to provide a removable nozzle member which may be assembled with a syringe body for the oral administration of liquid medicine, which member includes an elongate tube connected to a lip abutment skirt. The elongate tube is adaptable for insertion into a patient's mouth, and the lip abutment skirt prevents an individual's mouth from contacting and contaminating the syringe barrel.

Another object of the present invention is to provide a syringe body and nozzle member assembly which may be readily separated one from the other by application of digital pressure against the lip abutment skirt.

A further object of the present invention is to provide a nozzle member which will frictionally engage a tip on the syringe body in such a manner that when assembled, the nozzle member will not become inadvertently disengaged. A predetermined amount of digital pressure must be applied against the lip abutment skirt in order for removal of the member to occur.

BRIEF DESCRIPTION OF THE DRAWINGS

Novel features of the improved syringe in accordance with the present invention will be more readily understood from a consideration of the following description taken together with the accompanying drawings, in which a preferred embodiment is illustrated with the various parts thereof identified by suitable reference characters in each of the views, and in which.

DETAILED DESCRIPTION OF THE INVENTION

Figure 1:
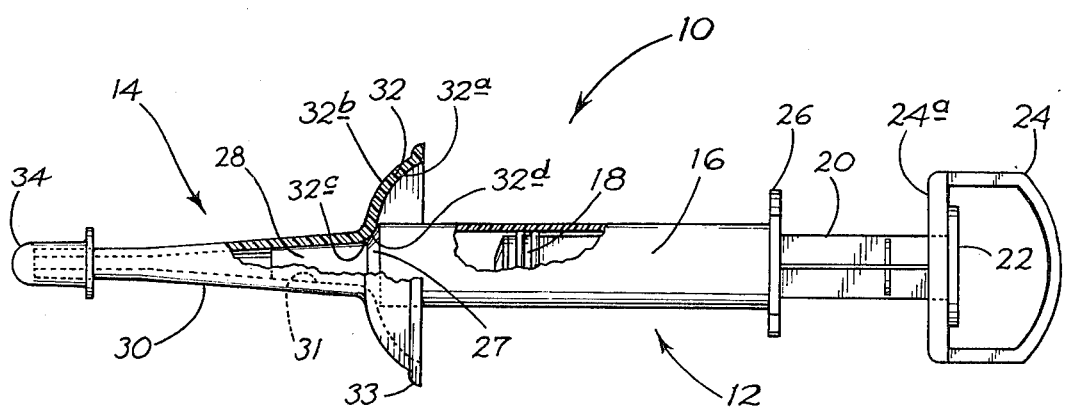
FIG. 1 is a side view, partially cut away, illustrating an oral syringe including a syringe body having a nozzle member mounted thereon according to an embodiment of the present invention.

Turning now to the drawings, there is illustrated in FIG. 1 an oral syringe generally indicated at 10. The assembly 10 includes a syringe body 12 and a nozzle member 14. Syringe body 12 includes an elongate barrel 16 within which is slidably disposed a piston 18. The piston 18 is reciprocable within the barrel 16 by means of a plunger 20.

The plunger 20 is provided with a thumb rest 22 and a ring 24. The ring 24 includes a base 24a having an aperture through which the plunger 20 is insertable. The ring 24 is sized such that an individual's thumb or finger may be inserted between the thumb rest 22 and the outer portion of the ring 24. Opposed finger grips are illustrated at 26 and provide a surface under which fingers may be placed in order to permit pressure to be applied against the thumb rest 22 for reciprocating the plunger 20.

At an end opposite to the finger grips 26, barrel 16 tapers at a relatively sharp angle, in a region indicated at 27. Tapered region 27 joins an elongate, hollow tip 28. The outer or exterior surface of tip 28 tapers at a slighter angle progressing away from the barrel, and is insertable within the nozzle member 14. Nozzle member 14 includes an elongate tube 30 which is integrally formed with a lip abutment skirt 32. Tube 30 includes a tapered internal or interior surface 31 over at least a portion of its length. Tube 30 receives tip 28 within interior surface 31 so that contact between the exterior surface of the tip and the interior surface provides sufficient frictional engagement for joining nozzle member 14 to barrel 16. Skirt 32 is generally funnel-shaped, and includes a generally concave inner surface 32a and a convex outer surface 32b. Skirt 32 is provided with an orifice 32c communicating with the interior of tube 30 which permits insertion of tip 28 into the tube.

The aforementioned frictional fit between the tip 28 and the tube 30 prevents inadvertent disassembly. Additionally, tapered region 27 of the barrel 16 may be at least partially inserted in aperture 32c to increase the frictional fit and thereby substantially decrease the event of accidental removal. Orifice 32c is provided with a curve or bevel 32d to facilitate fit against tapered region 27.

Figure 2:
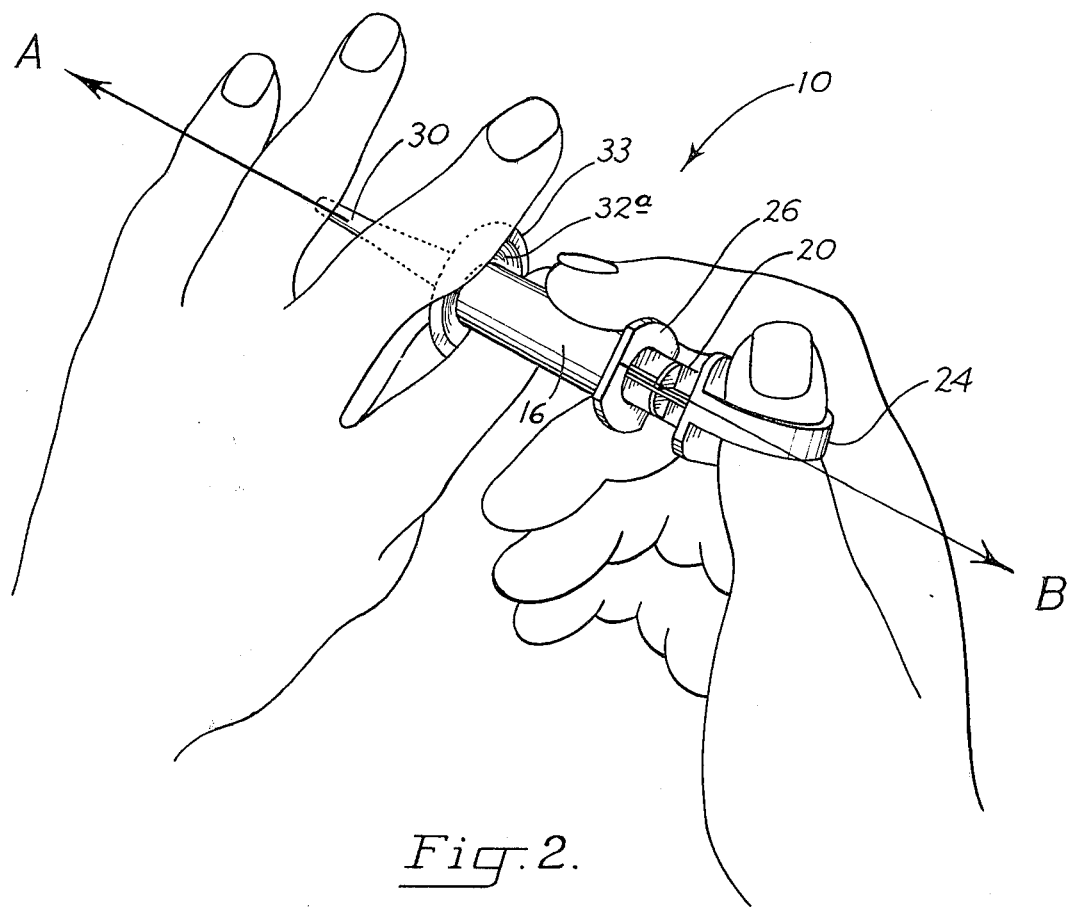
FIG. 2 is a perspective view illustrating typical placement of a person's hands as is done to effectuate removal of the nozzle member from the syringe body.

Lip abutment skirt 32 is also provided with a peripheral rim 33 which gives a certain amount of rigidity necessary to provide a support against which digital pressure is applied during removal of nozzle member 14 (see FIG. 2). Also, rim 33 provides an additional obstacle for preventing an individual's mouth from contacting the barrel 16.

A removable cap 34 is provided which fits tightly over the end of tube 30 for protection of such end when the device is not in use.

The syringe body, i.e. barrel 16 and tip 28, ordinarily is made of a rigid or semi-rigid plastic material for ease of handling. Nozzle member 14, on the other hand, is made of a more flexible material, such as a more flexible plastic or elastomer. This imparts flexibility to tube 30, which reduces the chance of inadvertent injury to the patient's mouth when the syringe is used. It also facilitates tube 30 to make a conforming fit with tip 28 when the nozzle member is mounted over the tip and the end of the barrel.

Use of the syringe will now be described. When it is desired to administer liquid medicine into the mouth of an individual, the nozzle member 14 and the syringe 12 are assembled, with tip 28 snugly inserted within tube 30. Cap 34 is removed, and plunger 20 is depressed, to place piston 18 adjacent the end of barrel 16 opposite the end having finger grips 26. Tube 30 may then be inserted into a vial of liquid medicine, and plunger 20 retracted toward the finger grips 26, to draw the liquid within barrel 16.

After a predetermined amount of liquid medicine has been drawn into the barrel 16, tube 30 is withdrawn from the vial and inserted into the mouth, between the cheek and lower teeth. Plunger 20 may then be depressed, which injects the medicine into the mouth.

Funnel-shaped lip abutment skirt 32 prevents the mouth of an individual to whom the medicine is being administered from contacting barrel 16.

After the oral administration of medicine, it may be desired to remove nozzle member 14 for cleaning. With attention now directed to FIG. 2, it can be seen that nozzle member 14 may be readily removed by the application of digital pressure in the direction of arrows A and B. For instance, the index finger and forefinger of a person's left hand may be placed about barrel 16 and against skirt 32. The fingers of the right hand are placed underneath the finger grips 26, and digital pressure is directed generally in the direction of the aforementioned arrows A and B. Such digital pressure will release engagement of tip 28 from portion 31 of the tube 30. It can be appreciated that during such removal, no contamination of barrel 16 or tip 28 need occur. Thus, syringe body 12 may be equipped with another nozzle member for the oral admininstration of medicine. The previously used nozzle member may be discarded, or cleaned.

From the above, it can be appreciated that the present invention provides several important advantages. The nozzle member is readily removed for cleaning purposes, thus freeing syringe body 12 for subsequent use. The flexibility of tube 30 and skirt 32 prevents injury to the mouth area, and may substantially alleviate apprehension in receiving medicine. The tapered interior of tube 30 permits snug frictional engagement with tapered tip 28.

While the invention has been particularly shown and described with reference to the foregoing preferred embodiment, it will be understood by those skilled in the art that other changes in form and detail may be made therein without departing from the spirit and scope of the invention as defined in the appended claims.

It is claimed and desired to secure by Letters Patent:

1. A syringe for the oral administration of a liquid comprising:
    an elongate hollow barrel for holding a dosage of liquid, said barrel having an elongate hollow tip extending from one end thereof, said tip having an average cross-sectional area less than the cross-sectional area of said barrel;
    a reciprocating plunger operatively connected to a piston slidably received within said barrel; and
    a removable nozzle member including an elongate tube integrally formed at one end with a lip abutment skirt, said skirt including an orifice which communicates with the interior surface of said tube, said orifice sized to receive said tip with said tip extending therethrough and at least partially into said tube so that contact between the exterior surface of said tip and the interior surface of said tube provides frictional engagement for joining said nozzle member to said hollow barrel, said skirt being dimensioned to extend radially outwardly from the periphery of said tube and said barrel and thereby presenting an obstacle preventing lip contact with said barrel when the opposite end of said tube is orally inserted.

2. The syringe as defined in claim 1, wherein the interior of said tube tapers progressing from the tube's said one end to the tube's said opposite end.

3. The syringe as defined in claim 2, wherein the exterior surface of said barrel tip tapers progressing away from said barrel.

4. The syringe as defined in claim 1, wherein said barrel is provided with a tapered end region adjacent said tip, said tapered end region being at least partially received within said orifice.

5. The syringe as defined in claim 1 wherein said skirt has a generally convex surface presented toward the tube's said opposite end and a generally concave surface presented toward said barrel.

6. The syringe as defined in claim 5 wherein an annular ring is disposed adjacent the outer periphery of said skirt.

7. The syringe as defined in claim 1 wherein said tube and said skirt are constructed of a material having greater flexibility than the material of which said barrel and tip are made.

* * * * *